(12) United States Patent
Lee et al.

(10) Patent No.: US 8,168,646 B2
(45) Date of Patent: May 1, 2012

(54) 3,4-DIHYDROQUINAZOLINE DERIVATIVES

(75) Inventors: Jae Yeol Lee, Seoul (KR); Dong Joon Choo, Seoul (KR); Young Deuk Kim, Gyeonggi-do (KR); Chun Rim Oh, Seoul (KR)

(73) Assignee: Dongwoo Syntech Co., Ltd., Chungbuk (KR)

( * ) Notice: Subject to any disclaimer, the term of this patent is extended or adjusted under 35 U.S.C. 154(b) by 178 days.

(21) Appl. No.: 12/598,734

(22) PCT Filed: May 6, 2008

(86) PCT No.: PCT/KR2008/002529
§ 371 (c)(1),
(2), (4) Date: Nov. 9, 2009

(87) PCT Pub. No.: WO2008/136631
PCT Pub. Date: Nov. 13, 2008

(65) Prior Publication Data
US 2010/0120803 A1     May 13, 2010

(30) Foreign Application Priority Data

May 8, 2007   (KR) ................. 10-2007-0044655
Aug. 30, 2007 (KR) ................. 10-2007-0087583

(51) Int. Cl.
*A61K 31/517* (2006.01)
(52) U.S. Cl. .................... 514/266.4; 544/292
(58) Field of Classification Search .......... 544/292
See application file for complete search history.

(56) References Cited

U.S. PATENT DOCUMENTS

2005/0197351 A1   9/2005 Lee et al.
2008/0070864 A1   3/2008 Martin et al.

FOREIGN PATENT DOCUMENTS

EP   1568695 A1   8/2005
WO   03/076418 A1   9/2003

OTHER PUBLICATIONS

Seo et al. "Discovery of potent T-type calcium channel blocker". 2007, Bioorganic & Medicinal Chemistry Letters, 17, 5740-5743.*
European Search Report issued in corresponding EP Application No. 08753326.1, dated Jul. 7, 2010.
Choi et al., "Synthesis and Biological Evaluation of Novel T-Type Calcium Channel Blockers," Bioorganic & Medicinal Chemistry Letters, 2007, vol. 17, pp. 471-475.
McCalmont et al., "Investigation into the Structure-Activity Relationship of Novel Concentration Dependent, Dual Action T-Type Calcium Channel Agonists/Antagonists," Bioorganic & Medicinal Chemistry, 2005, vol. 13, pp. 3821-3839.
Jae Yeol Lee, et al., "Growth inhibition of human cancer cells in vitro by T-type calcium channel blockers", Bioorganic & Medicinal Chemistry Letters, 2006, pp. 5014-5017, vol. 16.
Seong Jun Park, et al., "Synthesis and SAR studies of a novel series of T-type calcium channel blockers", Bioorganic & Medicinal Chemistry, 2006, pp. 3502-3511, vol. 14.
Hyewhon Rhim, et al., "Synthesis and biological activity of 3,4-dihydroquinazolines for selective T-type $Ca^{2+}$ channel blockers", Bioorganic & Medicinal Chemistry Letters, 2005, pp. 283-286, vol. 15.

* cited by examiner

*Primary Examiner* — James O Wilson
*Assistant Examiner* — Brian McDowell
(74) *Attorney, Agent, or Firm* — Sughrue Mion, PLLC

(57) ABSTRACT

Disclosed are 3,4-dihydroquinazoline derivatives of formula (I), a process of preparing them and a pharmaceutical composition including them. The 3,4-dihydroquinazoline derivatives of the present invention have excellent T-type calcium channel blocking effect and anti-cancer activity (I)

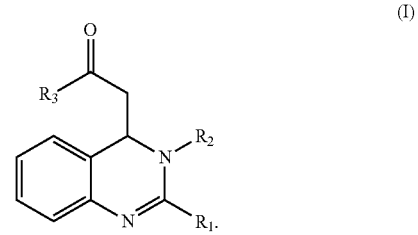

3 Claims, No Drawings

3,4-DIHYDROQUINAZOLINE DERIVATIVES

CROSS REFERENCE TO RELATED APPLICATIONS

This application is a National Stage of International Application Number PCT/KR2008/002529 filed May 6, 2008, claiming priority based on Korean Patent Application Numbers 10-2007-0044655 and 10-2007-0087583, filed May 8, 2007 and Aug. 30, 2007 respectively, the contents of all of which are incorporated herein by reference in their entirety.

TECHNICAL FIELD

The present invention relates to 3,4-dihydroquinazoline derivatives having excellent T-type calcium channel blocking effect and anti-cancer activity, a process of preparing them and a pharmaceutical composition including them.

BACKGROUND ART

Calcium plays a critical role as an intracellular signal, and controls many different cell processes, of which calcium appears to play an important role in cell growth [Berridge, M. J., et al., *Nat. Rev. Mol. Cell Biol.* 2003, 4, 517-529]. For example, it has also been shown that calcium signaling is required for cell cycle progression from G1/S phase through mitosis. It has been demonstrated that depletion of intracellular calcium arrests the cell cycle in the G0/G1 and S interphases [Clapham, D. E. *Cell* 1995, 80, 259-268]. Regulation of the changes in intracellular calcium has been proposed to be via a T-type calcium channel. Lined with this proposition, it has recently been reported that T-type calcium channel blockers (CCBs) inhibited cellular proliferation [McCalmont, W. F., et al., *Bioorg. Med. Chem. Lett.* 2004, 14, 3691-3695; McCalmont, W. F., et al., *Bioorg. Med. Chem.* 2005, 13, 3821-3839]. Opposed to T-type CCBs, however, it remains to discussion that some L-type CCBs as anti-hypertensive agents may be related to the risk of cancer in the elderly and promote growth of pre-existing cancer cells in human by inhibition of apoptosis [La Vecchia, C. et al., *Eur. J. Cancer* 2003, 39, 7-8]. Therefore, selective T-type CCBs could be another tool to treat cancer where the cell cycle has become aberrant.

On the other hand, it has been reported that over-expression of T-type calcium channel may cause epilepsy (Tsakiridou, E. et al., *J. Neurosci.* 1995, 15, 3110-3117), high blood pressure (Self, D. A. et al., *J Vacs. Res.* 1994, 31, 359-366), ventricular hypertrophy (Nuss, H. B. et al. , *Circ Res.* 1995, 73, 777-7825), pain (Shin, H. S. et al., *Science* 2003, 302, 117-119) and angina pectoris (Van der Vring, J. A. et al., *Am. J. Ther.* 1999, 6, 229-233). Therefore, selective T-type calcium channel blockers could be used for preventing or treating epilepsy, high blood pressure, ventricular hypertrophy, pain and angina pectoris.

DISCLOSURE OF INVENTION

Technical Problem

The present inventors have extensively studied to develop a novel compound for treating overgrowth diseases such as cancer via T-type calcium channel blocking. As a result, they discovered that a 3,4-dihydroquinazoline derivative of the following formula (I) has excellent T-type calcium channel blocking effect and anti-cancer activity.

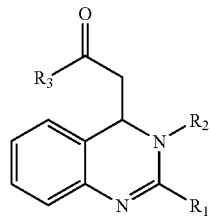

(I)

wherein, $R_1$, $R_2$ and $R_3$ are defined below.

An object of the present invention is, therefore, to provide a compound of the above formula (I) or pharmaceutically acceptable salt thereof.

Another object of the present invention is to provide a pharmaceutical composition comprising the compound of the above formula (I) or pharmaceutically acceptable salt thereof together with a pharmaceutically acceptable carrier.

Technical Solution

One aspect of the present invention relates to a compound of the following formula (I) or pharmaceutically acceptable salt thereof.

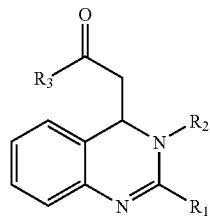

(I)

wherein, $R_1$ is $NR_4(CH_2)_nNR_5R_6$, wherein $R_4$ is hydrogen or $C_1$-$C_5$ alkyl, n is 4, 5 or 6, $R_5$ and $R_6$ are each independently hydrogen or $C_1$-$C_5$ alkyl, or taken together with the nitrogen atom to which they are attached form a 4 to 6-membered heterocycle;

$R_2$ is 4-biphenylyl;

$R_3$ is benzylamino, 4-aminobenzylamino or 4-fluorobenzenesulfoneaminobenzylamino.

In the above formula (I), $R_4$ is preferably $C_1$-$C_5$ alkyl, more preferably methyl or ethyl, and n is most preferably 5.

$R_5$ and $R_6$ are preferably identical and hydrogen or $C_1$-$C_5$ alkyl, more preferably methyl or ethyl; or taken together with the nitrogen atom to which they are attached form pyrrolidine or piperidine, more preferably pyrrolidine.

The term "$C_1$-$C_5$ alkyl" as used herein means a straight or branched hydrocarbon having 1 to 5 carbon atoms, which includes methyl, ethyl, n-propyl, i-propyl, n-butyl, i-butyl, t-butyl, etc. but is not limited thereto.

The most preferable compound among the compounds of the present invention is selected from the following group.

4-(N-benzylacetamino)-3-(4-biphenylyl)-2-[N-(5-pyrrolidin-1-ylpentyl)-N-methylamino]-3,4-dihydroquinazoline;

4-(N-benzylacetamino)-3-(4-biphenylyl)-2-[N-(5-N',N'-dimethylaminopentyl)-N-methylamino]-3,4-dihydroquinazoline; and 4-(N-benzylacetamino)-3-(4-biphenylyl)-2-[N-(5-aminopentyl)-N-methylamino]-3,4-dihydroquinazoline.

The processes for preparing the compounds according to the present invention are depicted in the following Reaction Schemes 1 to 5. However, those illustrated in the following Reaction Schemes represent only typical processes used in the present invention. The manipulation order, reagents, reaction conditions, etc. may be changed without limit.

(5). Then, the compound (5) is reacted with lithium aluminum hydride in a suitable solvent to give N-methyl-N-[5-(pyrrolidin-1-yl)pentyl]amine (6).

[Reaction Scheme 1]

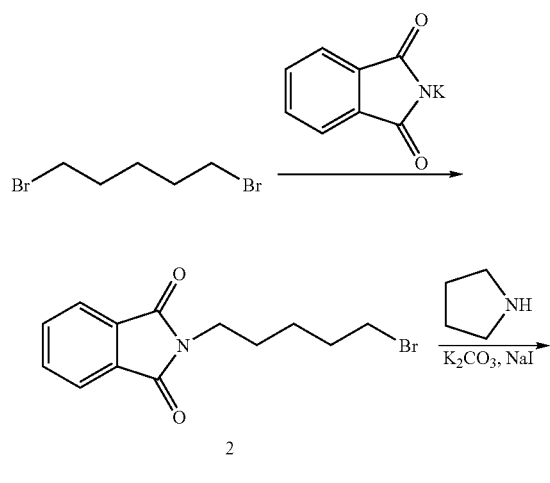

[Reaction Scheme 2]

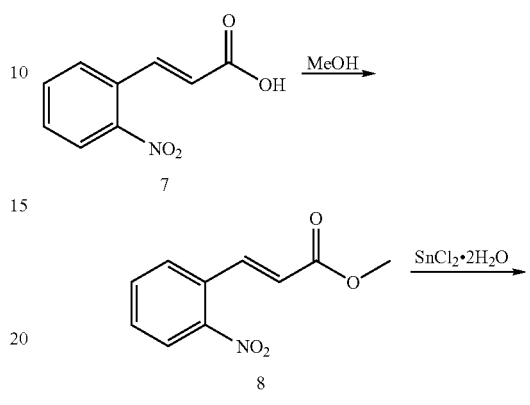

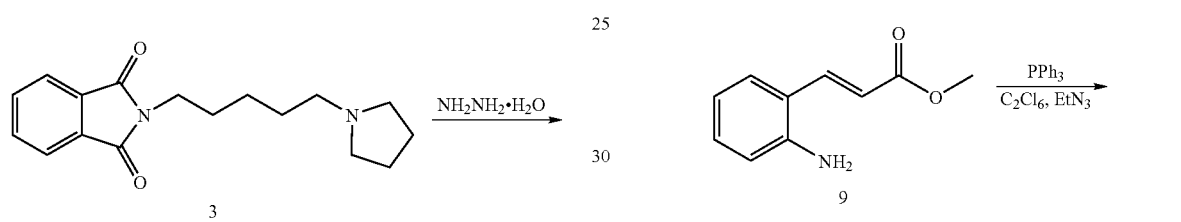

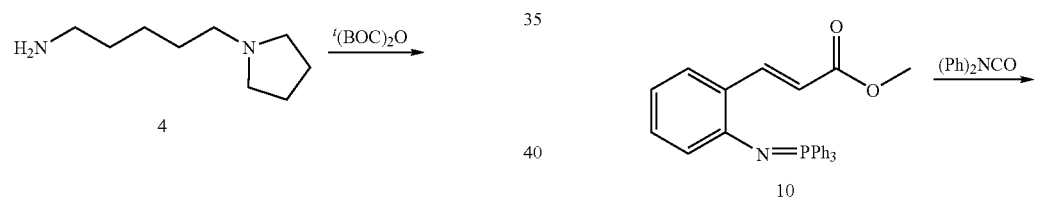

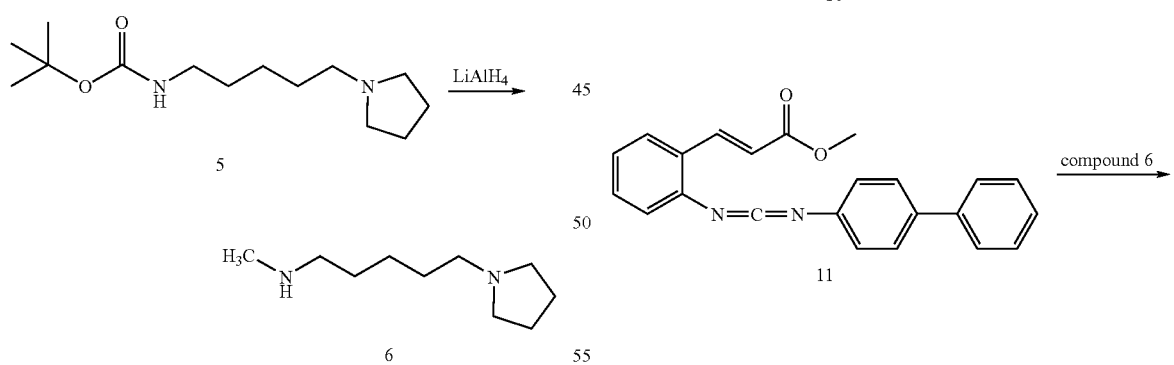

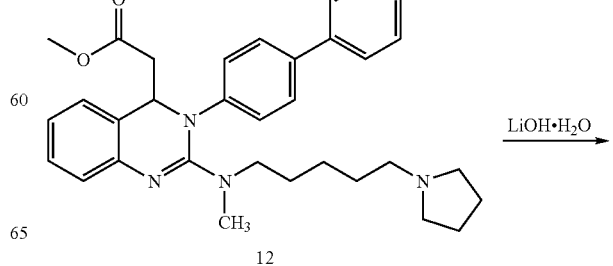

As shown in the above Reaction Scheme 1, 1,5-dibromopentane is reacted with potassium phthalimide in a suitable solvent to give N-(5-bromopentyl)phthalimide (2). The compound (2) is reacted with pyrrolidine in the presence of potassium carbonate and sodium iodide to give N-(5-pyrrolidin-1-ylpentyl)phthalimide (3). The compound (3) is reacted with hydrazine to provide 5-(pyrrolidin-1-yl)pentylamine (4). The compound (4) is reacted with di-t-butyl dicarbonate to give t-butyl (5-pyrrolidin-1-ylpentyl) carbamate

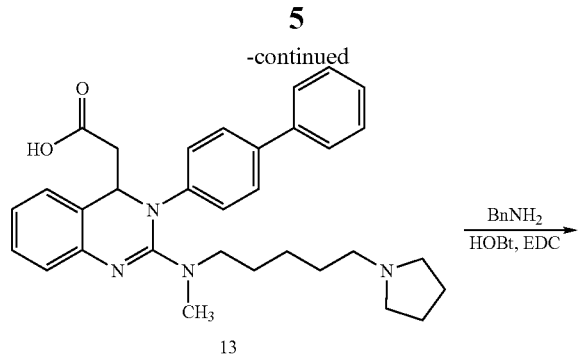

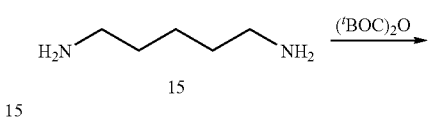

As shown in Reaction Scheme 2, compound (14) according to the present invention can be prepared using N-methyl-N-[5-(pyrrolidin-1-yl)pentyl]amine (6) obtained according to the above Reaction Scheme 1.

-nitrocinnamic acid (7) is reacted with methanol under acid catalyst to give methyl 2-nitrocinnamate (8), of which the nitro group is reduced preferably with $SnCl_2 \cdot 2H_2O$ to provide methyl 2-aminocinnamate (9). The compound (9) is reacted with triphenylphosphine, preferably in the presence of hexachloroethane and triethylamine to give methyl 3-[2-(triphenylphosphineimino)phenyl]acrylate (10). The compound (10) is reacted with 4-biphenylyl isocyanate in a suitable solvent to give methyl 3-[2-(4-biphenylyliminomethyleneamino)phenyl]acrylate (11). Then, the compound (11) is reacted with N-methyl-N-[5-(pyrrolidin-1-yl)pentyl]amine (6) obtained according to the above Reaction Scheme 1 in a suitable solvent to give 3-(4-biphenylyl)-2-[N-methyl-N-(5-pyrrolidin-1-ylpentyl)amino]-4-methoxycarbonylmethyl-3,4-dihydroquinazoline (12). This compound (12) is hydrolyzed preferably using LiOH/$H_2O$ to provide compound (13), which is reacted with benzylamine, preferably in the presence of 1-hydroxybenzotriazole (HOBT) and 1-[3-(dimethylamine)propyl]-3-ethylcarbodiimide hydrochloric acid (EDC) to give 4-(N-benzylacetamino)-3-(4-biphenylyl)-2-[N-(5-pyrrolidin-1-ylpentyl)-N-methylamino]-3,4-dihydroquinazoline (14).

[Reaction Scheme 3]

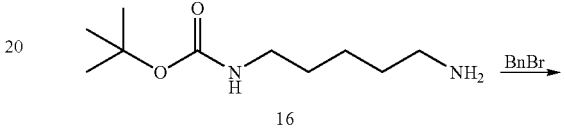

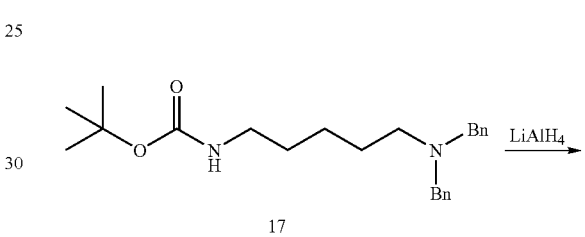

As shown in Reaction Scheme 3, compound (18) can be prepared as follows.

1,5-Diaminopentane (15) is reacted with di-t-butyl dicarbonate in a suitable solvent to give t-butyl (5-aminopentyl) carbamate (16), which is reacted with benzyl bromide in the presence of base to give t-butyl (5-dibenzylaminopentyl) carbamate (17). The obtained compound (17) is reacted with lithium aluminum hydride in a suitable solvent to give N,N-dibenzyl-N'-methylpentane-1,5-diamine (18).

[Reaction Scheme 4]

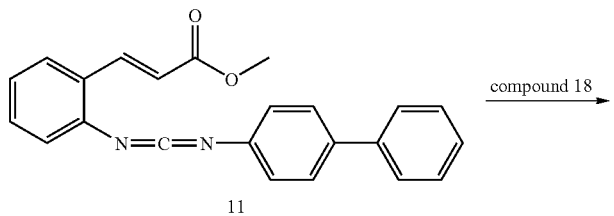

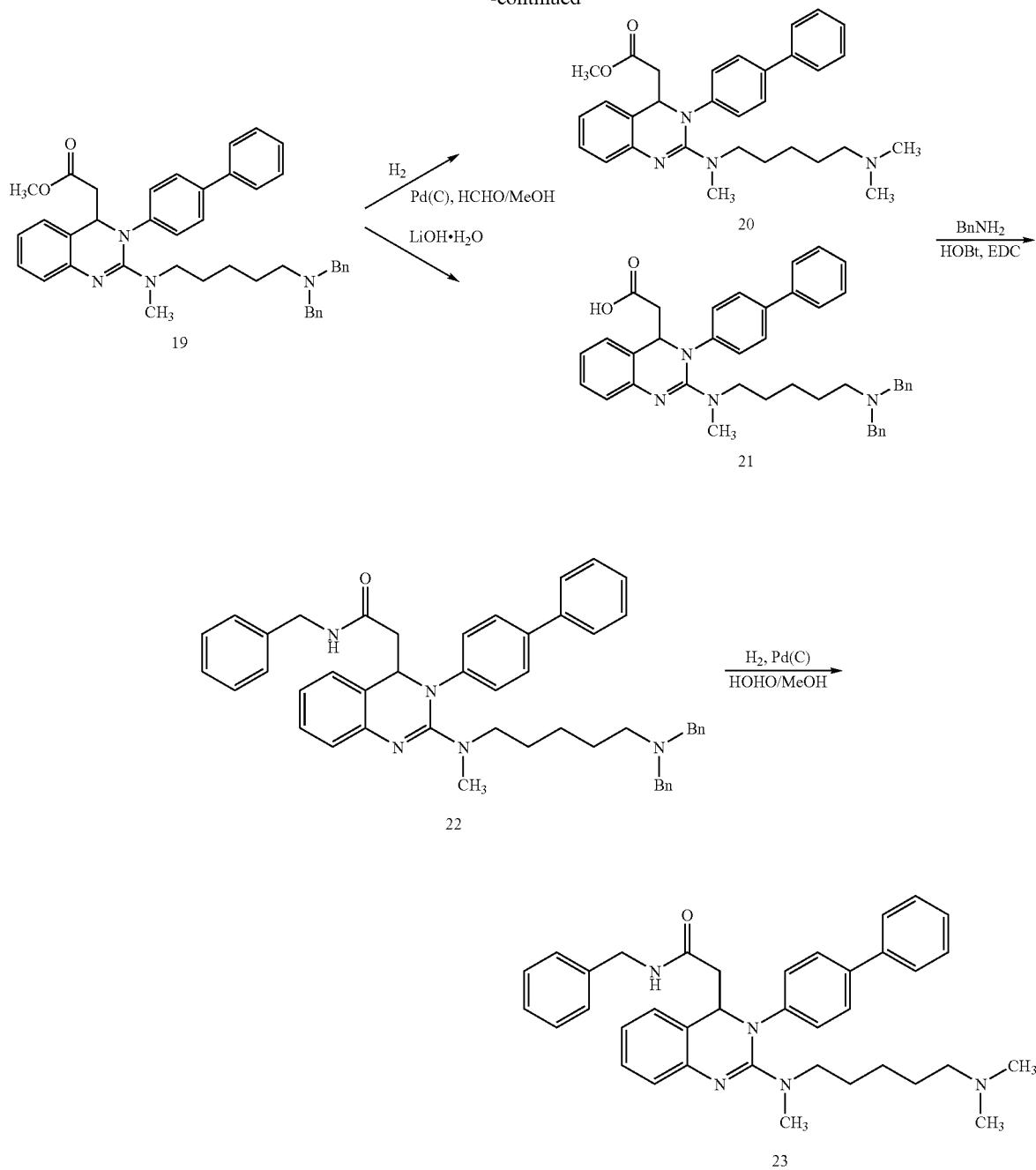

As shown in Reaction Scheme 4, compound (20) and compound (23) can be prepared using N,N-dibenzyl-N'-methyl-pentane-1,5-diamine (18) obtained according to the above Reaction Scheme 3 and methyl 3-[2-(4-biphenylyliminomethyleneamino)phenyl]acrylate (11) obtained according to the above Reaction Scheme 2.

Compound (11) is reacted with compound (18) in a suitable solvent to give 3-(4-biphenylyl)-2-[N-(5-dibenzylaminopentyl)-N-methylamino]-4-methoxycarbonylmethyl-3,4-dihydroquinazoline (19). Then, this compound (19) is hydrogenated in the presence of Pd(C) and formalin solution to give 2-[N-(5-N',N'-dimethylaminopentyl)-N-methylamino]-3-(4-biphenylyl)-4-methoxycarbonylmethyl-3,4-dihydroquinazoline (20).

On the other hand, compound (19) is hydrolyzed preferably using LiOH/H₂O to give compound (21), which is reacted with benzylamine, preferably in the presence of 1-hydroxybenzotriazole (HOBT) and 1-[3-(dimethylamine)propyl]-3-ethylcarbodiimide hydrochloric acid (EDC) to give N-benzyl-3-(4-biphenylyl)-2-[N-(5-N',N'-dibenzylaminopentyl)-N-methylamino]-3,4-dihydroquinazolin-4-ylacetamide (22). Then, the compound (22) is hydrogenated in the presence of Pd(C) and formalin solution to give 4-(N-benzylacetamino)-3-(4-biphenylyl)-2-[N-(5-N',N'-dimethylaminopentyl)-N-methylamino]-3,4-dihydroquinazoline (23).

[Reaction Scheme 5]

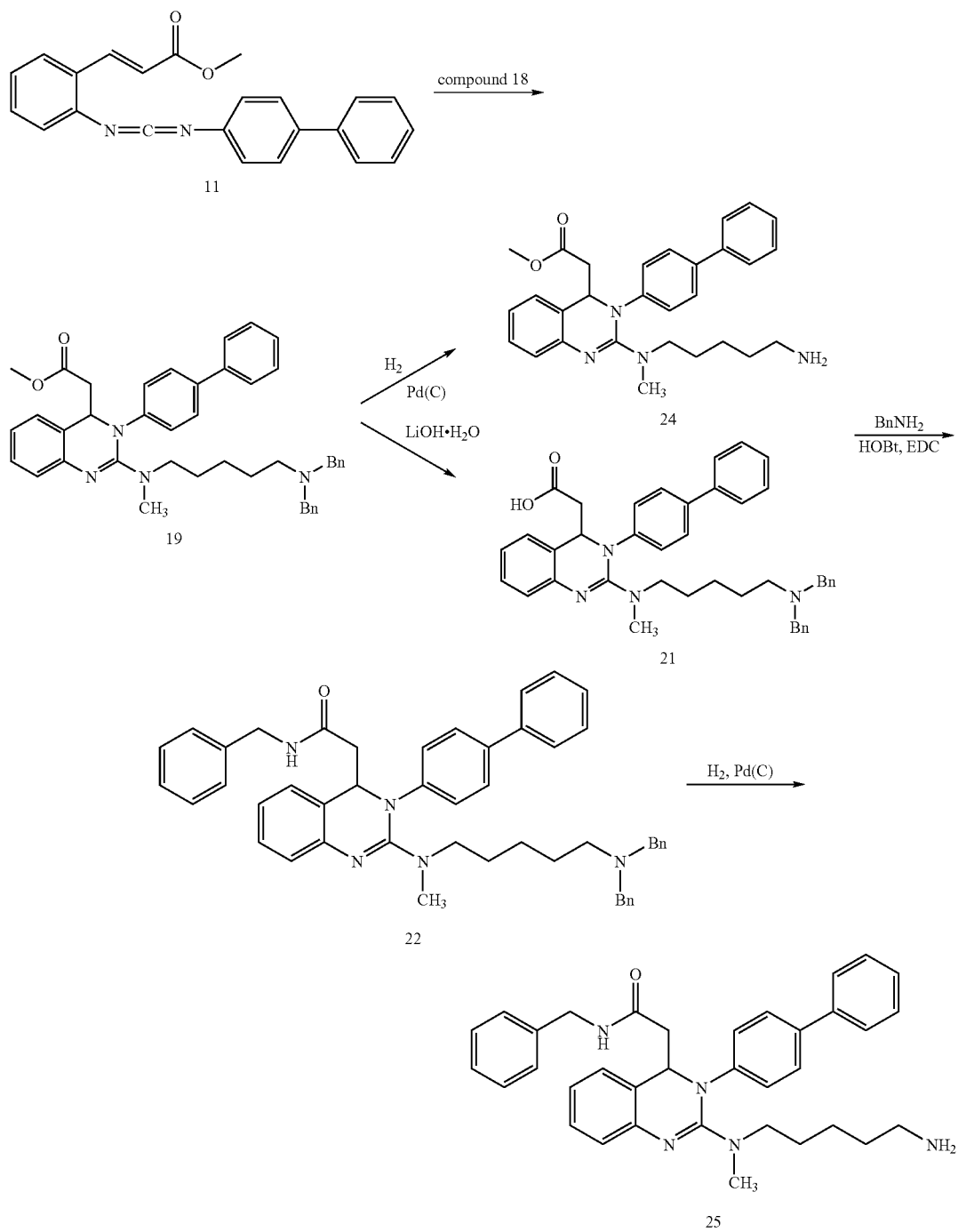

As shown in Reaction Scheme 5, compound (24) and compound (25) can be prepared using N,N-dibenzyl-N'-methyl-pentane-1,5-diamine (18) obtained according to the above Reaction Scheme 3 and methyl 3-[2-(4-biphenylyliminomethyleneamino)phenyl]acrylate (11) obtained according to the above Reaction Scheme 2. The specific process is the same as the above Reaction Scheme 4 except for using only Pd(C) catalyst instead of Pd(C) and formalin solution.

Another aspect of the present invention relates to a pharmaceutical composition comprising the compound of the above formula (I) or pharmaceutically acceptable salt thereof together with a pharmaceutically acceptable carrier. In particular, the pharmaceutical composition of the present invention can be used for treating cancer, especially colon cancer; or for preventing or treating epilepsy, high blood pressure, ventricular hypertrophy, pain or angina pectoris.

The pharmaceutical composition according to the present invention can be administered orally, e.g., ingestion or inhalation; or parenterally, e.g., injection, deposition, implantation or suppositories. The injection can be, for example, intravenous, intradermal, subcutaneous, intramuscular or intraperitoneal. Depending on the route of administration, the pharmaceutical composition of the present invention may be formulated as tablets, capsules, granules, fine subtilae, powders, sublingual tablets, suppositories, ointments, injection solutions, emulsions, suspensions, syrups, aerosols, etc. The above various forms of the pharmaceutical composition of the present invention can be prepared in a manner well known in the art using a pharmaceutically acceptable carrier(s) which are usually used for each form. Examples of the pharmaceutically acceptable carriers include excipient, binder, disintegrating agent, lubricant, preservative, antioxidant, isotonic agent, buffer, coating agent, sweetening agent, dissolvent, base, dispersing agent, wetting agent, suspending agent, stabilizer, colorant, etc.

The pharmaceutical composition of the present invention contains 0.01 to 100 wt % of a 3,4-dihydroquinazoline derivative of the above formula (I) or pharmaceutically acceptable salt thereof depending on the form thereof.

The specific dosage of the present pharmaceutical composition can be varied with species of mammals including a human-being, body weight, gender, severity of disease, judgment of doctor, etc. It is preferable that 0.01 to 50 mg of the active ingredient is administered per kg of body weight a day for oral use, while 0.01 to 10 mg of the active ingredient is administered per kg of body weight a day for parenteral use. The total daily dosage can be administered once or over several times depending on the severity of disease, judgment of doctor, etc.

Advantageous Effects

The 3,4-dihydroquinazoline derivatives of the present invention have excellent T-type calcium channel blocking effect and anti-cancer activity. Therefore, the compounds of the present invention can be used as new chemical therapy for treating overgrowth diseases such as cancer via T-type calcium channel blocking. Also, the compounds of the present invention can be used for preventing or treating epilepsy, high blood pressure, ventricular hypertrophy, pain or angina pectoris.

Best Mode for Carrying Out the Invention

The present invention is further illustrated by the following examples, which are not to be construed to limit the scope of the invention.

Example 1

Preparation of N-(5-Bromopentyl)Phthalimide (2)

To a solution of 1,5-dibromopentane (9.00 ml, 65.22 mmol) dissolved in DMF (100 ml) was added potassium phthalimide (12.08 g, 65.22 mmol) at room temperature, and the reaction mixture was stirred for 24 hours. After the reaction was completed, distilled water was added, and the resulting reaction mixture was stirred for 10 minutes and extracted with ethyl acetate three times. Then, the organic phase was washed with a saline solution, dried with anhydrous magnesium sulfate and distilled under reduced pressure. The resulting residue was subjected to silica gel column chromatography (eluent: ethyl acetate:hexane=1:3) to give the target compound (10.6 g, 55%).

$^1$H-NMR (400 MHz, CDCl$_3$) δ 7.85-7.70 (m, 4H, aromatic), 3.71-3.67 (t, 2H, —CH, —CH$_2$—CH$_2$—CH$_2$—CH$_2$—Br), 3.4-3.38 (t, 2H, —CH$_2$—CH$_2$—CH$_2$—CH$_2$—CH$_2$≦Br), 1.94-1.87 (m, 2H, —CH$_2$—CH$_2$—CH$_2$—CH$_2$—CH$_2$—Br), 1.73-1.67 (m, 2H, —CH$_2$—CH$_2$—CH$_2$—CH$_2$—CH$_2$—Br), 1.53-1.47 (m, 2H, —CH$_2$—CH$_2$—CH$_2$—CH$_2$—CH$_2$—Br).

Example 2

Preparation of N-(5-Pyrrolidin-1-ylpentyl)Phthalimide (3)

Potassium carbonate (13.57 g, 98.20 mmol), pyrrolidine (4.47 ml, 54.01 mmol) and sodium iodide (7.359 g, 49.098 mmol) were added to ethanol/acetone (1:1) at room temperature and stirred for 1 hour. To the reaction mixture was slowly added N-(5-bromopentyl)phthalimide (2) (10.60 g, 49.10 mmol), and the resulting reaction mixture was refluxed at 50° C. for 24 hours. After the reaction was completed, the resulting white solid was filtered and the solvent was evaporated under reduced pressure. Afterwards, the obtained residue was extracted with a saturated 1N NaOH aqueous solution and dichloromethane three times. Then, the organic phase was dried with anhydrous magnesium sulfate and distilled under reduced pressure. The resulting residue was subjected to silica gel column chromatography (eluent: dichloromethane: methnol:ammonia water=100:9:1) to give the target compound (3.27 g, 45%).

$^1$H-NMR (400 MHz, CDCl$_3$) δ 7.81-7.66 (m, 4H, aromatic), 3.66-3.63 (t, 2H, —CH$_2$—(CH$_2$)$_4$—NC$_4$H$_8$), 2.51-2.49 (t, 4H, —(CH$_2$)$_5$—NC$_2$H$_4$C$_2$H$_4$), 2.45-2.41 (m, 4H, —(CH$_2$)$_5$—NC$_2$ H$_4$C$_2$H$_4$), 1.77-1.74 (m, 2H, —(CH$_2$)$_4$—CH$_2$—NC$_4$H$_8$), 1.68-1.55 (m, 4H, —CH$_2$—CH$_2$—CH$_2$—CH$_2$—CH$_2$—NC$_4$H$_8$), 1.36-1.32 (m, 2H, —CH$_2$—CH$_2$—CH$_2$—CH$_2$—CH$_2$—NC$_4$H$_8$).

Example 3

Preparation of 5-(Pyrrolidin-1-yl)Pentylamine (4)

To a solution of N-(5-pyrrolidin-1-ylpentyl)phthalimide (3) (3.27 g, 11.42 mmol) dissolved in ethanol (100 ml) was added NH$_2$NH$_2$.H$_2$O (hydrazine monohydrate) (5.54 ml, 114.19 mmol) at room temperature, and the reaction mixture was refluxed for 24 hours. After the reaction was completed, the resulting reaction mixture was filtered under reduced pressure to give the target compound (1.50 g, 84%).

$^1$H-NMR (400 MHz, CDCl$_3$) δ 4.28 (br s, 2H, H$_2$N—), 2.69-2.66 (t, 2H, —CH$_2$—(CH$_2$)$_4$—NC$_4$H$_8$), 2.51 (s, 4H, —(CH$_2$)$_5$—NC$_2$H$_4$C$_2$H$_4$), 2.46-2.42 (t, 2H, —(CH$_2$)$_4$—CH$_2$—NC$_4$H$_8$), 1.73 (s, 4H, —(CH$_2$)$_5$—NC$_2$H$_4$C$_2$H$_4$), 1.52-1.43 (m, 4H, —CH$_2$—CH$_2$—CH$_2$—CH$_2$—CH$_2$—NC$_4$H$_8$), 1.33-1.25 (m, 2H, —CH$_2$—CH$_2$—CH$_2$—CH$_2$—CH$_2$—NC$_4$H$_8$).

$^{13}$C-NMR (CDCl$_3$) δ 56.18, 54.06, 41.30, 31.92, 28.22, 24.68, 23.31.

Example 4

Preparation of t-butyl (5-Pyrrolidin-1-ylpentyl) Carbamate (5)

5-(pyrrolidin-1-yl)pentylamine (4) (1.50 g, 9.60 mmol) was added to 50 ml of flask, which was then evacuated and equipped with a nitrogen balloon. Afterwards, dichloromethane (30 ml) was added to dissolve the compound (4) and di-t-butyl dicarbonate (2.64 ml, 11.52 mmol) was slowly added at 0° C. Then, dichloromethane (20 ml) was further added and stirred for 24 hours. After the reaction was completed, the reaction mixture was basified with a saturated 1N NaOH aqueous solution to pH 10-11 and extracted with dichloromethane three times. Then, the organic phase was dried with anhydrous magnesium sulfate and distilled under reduced pressure. The resulting residue was subjected to silica gel column chromatography (eluent: dichloromethane: methnol:ammonia water=40:7:1) to give the target compound (1.5 g, 65%).

$^1$H-NMR (400 MHz, CDCl$_3$) δ 4.63 (br s, 1H, —NH—), 3.07-3.06 (t, 2H, —CH$_2$—(CH$_2$)$_4$—NC$_4$H$_8$), 2.51 (s, 4H, —NC$_2$H$_4$C$_2$H$_4$), 2.45-2.41 (m, 2H, —(CH$_2$)$_4$—CH$_2$—NC$_2$H$_4$C$_2$H$_4$), 1.76 (s, 4H, —(CH$_2$)$_5$—NC$_2$H$_4$C$_2$H$_4$), 1.54-1.28 (m, 15H, —CH$_2$—CH$_2$—CH$_2$—CH$_2$—CH$_2$—NC$_2$H$_4$C$_2$H$_4$, —C(CH$_3$)$_3$).

Example 5

Preparation of N-Methyl-N-[5-(Pyrrolidin-1-yl)Pentyl]amine (6)

To a solution of t-butyl (5-pyrrolidin-1-ylpentyl) carbamate (5) (1.59 g, 6.20 mmol) dissolved in dihydrofuran (100 ml) was added LiAlH$_4$ (lithium aluminum hydride) (2.35 g, 62.00 mmol), and the reaction mixture was stirred for 24 hours. To the resulting reaction mixture was added sodium potassium tartrate (17.5 g, 62.0 mmol) for quenching, and the mixture was filtered with celite. The solvent was evaporated under reduced pressure to give the target compound (0.7 g, 66%).

$^1$H-NMR (400 MHz, CDCl$_3$) δ 2.63-2.47 (m, 8H, —CH$_2$—(CH$_2$)$_3$—CH$_2$—NC$_2$H$_4$C$_2$H$_4$), 2.45 (s, 3H, —NH—CH$_3$), 1.80-1.79 (m, 4H, —(CH$_2$)$_5$—NC$_2$H$_4$C$_2$H$_4$), 1.56-1.53 (m , 4H, —CH$_2$—CH$_2$—CH$_2$—CH$_2$—CH$_2$—NC$_4$H$_8$), 1.41-1.33 (m, 2H, —(CH$_2$)$_2$—CH$_2$—(CH$_2$)$_2$—NC$_4$H$_8$).

$^{13}$C-NMR (CDCl$_3$) δ 56.43, 54.05, 51.79, 36.14, 29.48, 28.70, 25.27, 23.19.

Example 6

Preparation of Methyl 2-Nitrocinnamate (8)

To a solution of 2-nitrocinnamic acid (7) (10.38 g, 53.76 mmol) dissolved in methanol (200 ml) was dropped a small amount of concentrated sulfuric acid at room temperature, and the reaction mixture was stirred at 70° C. for 12 hours. After the reaction was completed, the resulting solution was basified with a saturated aqueous solution of sodium bicarbonate to weak basicity and extracted with dichloromethane three times. Then, the organic phase was dried with anhydrous magnesium sulfate and distilled under reduced pressure. The resulting residue was subjected to silica gel column chromatography (eluent: ethyl acetate:hexane=1:5) to give the target compound (11.03 g, 99%).

$^1$H-NMR (400 MHz, CDCl$_3$) δ 8.16-8.12 (d, 1H, —C—CH=CH—), 8.09-7.58 (m, 4H, aromatic), 6.43-6.37 (d, 1H, —C—CH=CH—), 3.86 (s, 3H, —OCH$_3$).

Example 7

Preparation of Methyl 2-Aminocinnamate (9)

To a solution of methyl 2-nitrocinnamate (8) (11.03 g, 53.24 mmol) in ethyl acetate (200 ml) was added SnCl$_2$.H$_2$O (60.06 g, 266.19 mmol) at room temperature, and the resulting solution was stirred at 70° C. for 60 minutes. After the reaction was completed, the solution was allowed to cool to room temperature, basified with a saturated aqueous solution of sodium bicarbonate to weak basicity, and filtered with celite. The aqueous phase was extracted with ethyl acetate three times, and the combined organic phase was dried with anhydrous magnesium sulfate and distilled under reduced pressure. The resulting residue was subjected to silica gel column chromatography (eluent: ethyl acetate:hexane=1:5) to give the target compound (8.50 g, 90%).

$^1$H-NMR (400 MHz, CDCl$_3$) δ 7.92-7.86 (d, 1H, —C—CH=CH—), 7.44-6.76 (m, 4H, aromatic), 6.42-6.36 (d, 1H, —C—CH=CH—), 3.83 (s, 3H, —OCH$_3$).

Example 8

Preparation of Methyl 3-[2-(Triphenylphosphineimino)Phenyl] Acrylate (10)

To a solution of methyl 2-aminocinnamate (9) (8.93 g, 50.40 mmol) in toluene (200 ml) was dropped triphenylphosphine (19.83 g, 75.59 mmol) and hexachloroethane (17.90 g, 75.59 mmol). Then, to the reaction mixture was slowly dropped triethylamine (3.24 ml, 23.3 mmol) at room temperature, and the resulting reaction mixture was refluxed for 3 hours. After the reaction was completed, the solution was allowed to cool to room temperature and filtered with celite. The resulting solution was extracted with dichlormethane three times, and the combined organic phase was dried with anhydrous magnesium sulfate and distilled under reduced pressure. The resulting residue was subjected to silica gel column chromatography (eluent: ethyl acetate:hexane:dichloromethane=1:3:1) to give the target compound (22.05 g, quantitative yield).

$^1$H-NMR (400 MHz, CDCl$_3$) δ 8.78-8.81 (d, 1H, —C—CH=CH—), 7.84-6.69 (m, 19H, aromatic), 6.42-6.53 (d, 1H, —C—CH=CH—), 3.84 (s, 3H, —OCH$_3$).

Example 9

Preparation of 3-[2-(4-Biphenylyliminomethyleneamino)Phenyl]Acrylate (11)

To a solution of methyl 3-[2-(triphenylphosphineimino) phenyl]acrylate (10) (22.05 g, 50.40 mmol) in toluene (300 ml) was added 4-biphenylyl isocyanate (9.84 g, 50.40 mmol). The reaction mixture was stirred at room temperature for 12 hours, distilled under reduced pressure, and recrystallized with methanol to give the target compound as a white solid (6.95 g, 64%).

$^1$H-NMR (400 MHz, CDCl$_3$) δ 8.17-8.13 (d, 1H, —C—CH=CH—), 7.61-7.25 (m, 13H, aromatic), 6.54-6.50 (d, 1H, —C—CH=CH—), 3.81 (s, 3H, —OCH$_3$).

Example 10

Preparation of 3-(4-Biphenylyl)-2-[N-Methyl-N-(5-Pyrrolidin-1-ylpentyl)Amino]-4-Methoxycarbonylmethyl-3,4-Dihydroquinazoline (12)

To a solution of 3-[2-(4-biphenylyliminomethyleneamino) phenyl]acrylate (11) (0.83 g, 2.35 mmol) in toluene (50 ml) was slowly added N-methyl-N-[5-(pyrrolidin-1-yl)pentyl] amine (6) obtained in Example 5 (0.80 g, 4.70 mmol) at 0° C., and the reaction mixture was stirred at room temperature for 1 hour. After the reaction was completed, the resulting reaction mixture was extracted with a saturated 1N NaOH aqueous solution and dichloromethane three times. Then, the combined organic phase was dried with anhydrous magnesium sulfate and distilled under reduced pressure. The resulting residue was subjected to silica gel column chromatography (eluent: dichloromethane:methnol:ammonia water=100:9:1) to give the target compound (0.63 g, 52%).

$^1$H-NMR (400 MHz, CDCl$_3$) δ 7.51-6.89 (m, 13H, aromatic), 5.1.(dd, J=4.5 and 10 Hz, 1H, —NH—CH—), 3.76 (s, 3H, —OCH$_3$), 2.85-2.48 (m, 11H, —N—CH$_3$, —CH$_2$—(CH$_2$)$_3$—CH$_2$—NC$_2$H$_4$C$_2$H$_4$), 1.88 (s, 4H, —(CH$_2$)$_5$—NC$_2$H$_4$C$_2$H$_4$), 1.66 (s, 2H, —CH$_2$—CH$_2$—(CH$_2$)$_3$—NC$_2$H$_4$C$_2$H$_4$), 1.53 (s, 2H, —(CH$_2$)$_3$—CH$_2$—CH$_2$—NC$_2$H$_4$C$_2$H$_4$), 1.26-1.22 (m, 2H, —CH$_2$—CH$_2$—CH$_2$—CH$_2$—CH$_2$—NC$_2$H$_4$C$_2$H$_4$).

$^{13}$C-NMR (CDCl$_3$) δ 171.88, 153.38, 145.38, 144.15, 140.30, 136.77, 128.76, 128.36, 127.85, 127.08, 126.73, 124.75, 122.86, 122.59, 122.12, 61.21, 56.30, 54.06, 53.45, 51.89, 39.54, 35.40, 30.90, 28.21, 27.16, 24.91, 23.37.

Example 11

Preparation of 4-(N-Benzylacetamino)-3-(4-Biphenylyl)-2-[N-(5-Pyrrolidin-1-ylpentyl)-N-Methylamino]-3,4-Dihydroquinazoline (14) (KYS05080)

To a solution of 3-(4-biphenylyl)-2-[N-methyl-N-(5-pyrrolidin-1-ylpentyl)amino]-4-methoxycarbonylmethyl-3,4-dihydroquinazoline (12) (0.53 g, 1.01 mmol) in dihydrofuran (20 ml) and water (20 ml) was added LiOH/H$_2$O (0.21 g, 5.05 mmol), and the reaction mixture was stirred at 70° C. for 2 hours. After the reaction was completed, the solution was allowed to cool to room temperature and the solvent was evaporated under reduced pressure. Then, the reaction mixture was acidified with 3N HCl to pH 3-4 and extracted with dichloromethane three times. The combined organic phase was dried with anhydrous magnesium sulfate and distilled under reduced pressure to give compound (13) as a white solid. To a solution of compound (13) and 1-hydroxybenzotriazole (HOBT) (0.881 g, 6.52 mmol) in dichloromethane/tetrahydrofuran (1:1, 40 ml) was dropped benzylamine (0.71 ml, 6.52 mmol) at 0° C., and the reaction mixture was stirred at 0° C. for 1 hour. Then, 1-[3-(dimethylamino)propyl]-3-ethylcarbodiimide hydrochloric acid (EDC) (1.0 g, 1.20 mmol) was added and stirred at room temperature for 12 hours. After the reaction was completed, the resulting reaction mixture was distilled under reduced pressure and dissolved in dichloromethane. Afterwards, the resulting solution was extracted with a 0.5M hydrochloric acid aqueous solution two times, a saturated aqueous solution of sodium bicarbonate two times and water one time, and washed with a saline solution. The organic phase was dried with anhydrous magnesium sulfate and distilled under reduced pressure. The resulting residue was subjected to silica gel column chromatography (eluent: dichloromethane:methnol:ammonia water=100:9:1) to give the target compound as a yellow liquid (0.33 g, 64%).

$^1$H-NMR (400 MHz, CDCl$_3$) δ 7.55-6.97 (m, 18H, aromatic), 5.33-5.29 (dd, J=5.3 and 9.4 Hz, 1H, —NH—CH—), 4.52-4.50 (m, 2H, C$_6$H$_5$—CH$_2$—), 3.41-3.16 (d, 2H, —CH$_2$—CH—), 2.70-2.62 (m, 4H, —(CH$_2$)$_5$—NC$_2$H$_4$C$_2$H$_4$, 2.46-2.37 (m, 7H, —CH$_2$—CH$_2$—CH$_2$—CH$_2$—CH$_2$—NC$_4$H$_8$—NCH$_3$), 1.96-1.95 (m, 4H, —(CH$_2$)$_5$—NC$_2$H$_4$C$_2$H$_4$), 1.74-1.25 (m, 6H, —CH$_2$—(CH$_2$)$_3$—CH$_2$—NC$_4$H$_8$).

$^{13}$C-NMR(CDCl$_3$) δ 170.26, 154.01, 145.47, 143.89, 140.41, 138.53, 136.75, 128.77, 128.58, 128.05, 127.78, 127.40, 127.07, 126.77, 126.35, 125.08, 122.97, 122.33, 122.21, 61.17, 56.55, 55.44, 54.23, 49.81, 43.72, 41.63, 35.46, 28.66, 27.06, 25.02, 23.38.

Example 12

Preparation of t-butyl (5-Aminopentyl) Carbamate (16)

To a solution of 1,5-diaminopentane (15) (1.14 ml, 9.79 mmol) in dichloromethane (100 ml) was added di-tert-butyl dicarbonate (1.12 ml, 4.90 mmol) at 0° C., and the resulting solution was stirred at room temperature for 12 hours. After the reaction was completed, H$_2$O was added to remove solid residue. The reaction mixture was basified with 1N NaOH aqueous solution to pH 10-11 and extracted with dichloromethane three times. Then, the combined organic phase was dried with anhydrous magnesium sulfate and distilled under reduced pressure. The resulting residue was subjected to silica gel column chromatography (eluent: dichloromethane:methnol:ammonia water=100:9:1) to give the target compound as a yellow liquid (1.00 g, 51%).

$^1$H-NMR (400 MHz, CDCl$_3$) δ 4.57 (br, 1H, —NH—), 3.11-3.09 (d, J=6.2 Hz, 2H, —NH—CH$_2$—), 2.71-2.67 (t, J=6.9 Hz, —CH$_2$—(Bn)$_2$), 1.78 (br, 2H, —NH$_2$), 1.51-1.44 (m, 4H, —NH—CH$_2$—CH$_2$—, —CH$_2$—CH$_2$—N—(Bn)$_2$), 1.42 (s, 9H, —O(CH$_3$)$_3$), 1.37-1.31 (m, 2H, —CH$_2$—CH$_2$—CH$_2$—).

Example 13

Preparation of t-butyl (5-Dibenzylaminopentyl) Carbamate (17)

To a solution of t-butyl (5-aminopentyl) carbamate (16) (1.00 g, 4.94 mmol) in dichloromethane (100 ml) was slowly dropped benzyl bromide (1.99 ml, 16.81 mmol) and sodium carbonate (2.24 g, 26.69 mmol) at room temperature. The resulting reaction mixture was stirred at 40° C. for 12 hours and extracted with dichloromethane three times. Then, the combined organic phase was dried with anhydrous magnesium sulfate and distilled under reduced pressure. The resulting residue was subjected to silica gel column chromatography (eluent: ethyl acetate:hexane:dichloromethane=1:10:1) to give the target compound as a yellow liquid (0.92 g, 49%).

$^1$H NMR (400 MHz, CDCl$_3$) δ 7.40-7.23 (m, 10H, aromatic), 3.57 (s, 4H, —(Bn)$_2$), 3.09-3.07 (m, 2H, HN—CH$_2$—), 2.44 (t, J=7.05 Hz, 2H, —CH$_2$—N—), 1.58-1.51 (m, 2H, HN—CH$_2$—CH$_2$—), 1.48 (s, 9H, (CH$_3$)$_3$C—O), 1.41-1.27 (m, 4H, HN—CH$_2$—CH$_2$—CH$_2$—CH$_2$—CH$_2$—).

Example 14

Preparation of N,N-Dibenzyl-N'-Methylpentane-1,5-Diamine (18)

To a solution of t-butyl (5-dibenzylaminopentyl) carbamate (17) (0.92 g, 2.41 mmol) in dihydrofuran (100 ml) was added lithium aluminum hydride (0.91 g, 24.1 mmol) at room temperature, and the reaction mixture was stirred at 70° C. for 12 hours. After the reaction was completed, the resulting solution was allowed to cool to room temperature and Rochelle's salt (6.79 g, 24.1 mmol) was added. Then, the reaction mixture was stirred for 8 hours and filtered with celite. The filtrate was extracted with dichloromethane three times, dried with anhydrous magnesium sulfate, and distilled under reduced pressure to give the target compound as a yellow liquid (0.42 g, 60%).

¹H NMR (400 MHz, CDCl₃) δ 7.42-7.22 (m, 10H, aromatic), 3.58 (s, 4H, —(Bn)₂), 2.52-2.44 (m, 5H, HN—CH₂—CH₂—CH₂—CH₂—CH₂—), 2.38 (s, 3H, —NH—CH₃), 1.57-1.53 (m, 2H, HN—CH₂—CH₂—CH₂—), 1.42-1.31 (m, 4H, HN—CH₂—CH₂—CH₂—CH₂—CH₂—).

¹³C NMR (400 MHz, CDCl₃) δ 139.9, 128.8, 128.1, 126.7, 58.4, 53.2, 51.7, 35.9, 29.1, 26.9, 24.8.

Example 15

Preparation of 3-(4-Biphenylyl)-2-[N-(5-Dibenzylaminopentyl)-N-Methylamino]-4-Methoxycarbonylmethyl-3,4-Dihydroquinazoline (19)

To a solution of methyl 3-[2-(4-biphenylyliminomethyleneamino)phenyl]acrylate (11) (1.12 g, 3.15 mmol) in toluene (100 ml) was added N,N-dibenzyl-N'-methylpentane-1,5-diamine (18) (1.87 g, 6.30 mmol). Then, the reaction mixture was stirred for 2 hours and extracted with dichloromethane three times. The combined organic phase was dried with anhydrous magnesium sulfate and distilled under reduced pressure. The resulting residue was subjected to silica gel column chromatography (eluent: ethyl acetate:hexane:dichloromethane=1:2:1) to give the target compound as a yellow liquid (2.56 g, quantitative yield).

¹H-NMR (400 MHz, CDCl₃) δ 7.51-7.01 (m, 23H, aromatic), 5.14-5.10 (dd, J=4.7 and 10.3 Hz, 1H, —CH₂—CH—N—), 3.75-3.71 (m, 5H, —OCH₃, —₃HCN—CH₂—), 3.57-3.58 (m, 4H, —(Bn)₂), 3.27-2.52 (m, 7H, —CO—CH₂—, —NCH₃, —CH₂—N(Bn)₂), 2.41 (m, 2H, —CH₂—CH₂—(CH₂)₃—N(Bn)₂), 1.51-1.45 (m, 4H, —(CH₂)₃—CH₂—CH₂—N(Bn)₂).

Example 16

Preparation of 2-[N-(5-N',N'- Dimethylaminopentyl)-N-Methylamino]-3-(4-Biphenylyl)-4-Methoxycarbonylmethyl-3,4-Dihydroquinazoline (20) (KYS05089)

To a solution of 3-(4-biphenylyl)-2-[N-(5-dibenzylaminopentyl)-N-methylamino]-4-methoxycarbonylmethyl-3,4-dihydroquinazoline (19) (430 mg, 0.33 mmol) and formalin solution (37%, 0.3 ml) in methanol (20 ml) was added 10% Pd(C) (110 mg), and the reaction mixture was stirred under hydrogen atmosphere for 24 hours. After the reaction was completed, the resulting reaction mixture was filtered with celite, extracted with dichloromethane three times and washed with a saline solution. The combined organic phase was dried with anhydrous magnesium sulfate and distilled under reduced pressure. The resulting residue was subjected to silica gel column chromatography (eluent: dichloromethane:methanol:ammonia water=100:9:1) to give the target compound as a yellow liquid (274 mg, 60%).

¹H-NMR (400 MHz, CDCl₃) δ 7.52-6.88 (13H, m, Ph), 5.11 (1H, dd, J=10.4 and 4.5 Hz, COCH₂CH), 3.75 (3H, s, OCH₃), 3.50 (1H, m, CH₃N—CH), 3.15 (1H, m, CH₃N—CH), 2.88-2.82 (4H, m, CH₃—N and COCH), 2.51 (1H, dd, J=15.5 and 4.6 Hz, COCH), 2.25-2.23 (2H, m, —NCH₂), 2.20 (6H, s, 2×N—CH₃), 1.52-1.45 (4H, m, 2×CH₂), 1.24-1.23 (2H, m, CH₂).

¹³C NMR (400 MHz, CDCl₃) δ 171.9, 153.4, 145.4, 144.2, 140.3, 136.8, 128.8, 128.4, 127.9, 127.1, 126.8, 125.4, 124.8, 122.9, 122.6, 122.1, 61.2, 59.7, 49.5, 45.2, 43.8, 41.8, 35.3, 27.1, 27.0, 24.7.

HRMS (FAB+) calcd for C₃₁H₃₉N₄O₂: [M+H]⁺= 499.3073, found=499.3060.

Example 17

Preparation of N-Benzyl-3-(4-Biphenylyl)-2-[N-(5-N',N'-Dibenzylaminopentyl)-N-Methylamino]-3,4-Dihydroquinazolin-4-ylacetamide (22)

To a solution of 3-(4-biphenylyl)-2-[N-(5-dibenzylaminopentyl)-N-methylamino]-4-methoxycarbonylmethyl-3,4-dihydroquinazoline (19) (2.56 g, 3.93 mmol) in dihydrofuran (50 ml) and water (50 ml) was added LiOH/H₂O (0.825 g, 19.7 mmol), and the reaction mixture was stirred at 70° C. for 2 hours. After the reaction was completed, the resulting solution was allowed to cool to room temperature and the solvent was evaporated under reduced pressure. Then, the resulting reaction mixture was acidified with 3N HCl to pH 3-4 and extracted with dichloromethane three times. The combined organic phase was dried with anhydrous magnesium sulfate and distilled under reduced pressure to give compound (21) as a white solid. To a solution of compound (21) and 1-hydroxybenzotriazole (HOBT) (1.00 g, 7.41 mmol) in dichloromethane/tetrahydrofuran (1:1, 40 ml) was dropped benzylamine (0.804 ml, 7.41 mmol) at 0° C., and the reaction mixture was stirred at 0° C. for 1 hour. Then, 1-[3-(dimethylamino)propyl]-3-ethylcarbodiimide hydrochloric acid (EDC) (1.21 g, 6.30 mmol) was added and stirred at room temperature for 12 hours. After the reaction was completed, the reaction mixture was distilled under reduced pressure and dissolved in dichloromethane. Afterwards, the resulting solution was extracted with a 0.5M hydrochloric acid aqueous solution two times, a saturated aqueous solution of sodium bicarbonate two times and water one time, and washed with a saline solution. The organic phase was dried with anhydrous magnesium sulfate and distilled under reduced pressure. The resulting residue was subjected to silica gel column chromatography (eluent: dichloromethane:methnol=15:1) to give the target compound as a yellow liquid (2.13 g, 79%).

¹H-NMR (400 MHz, CDCl₃) δ 7.63-7.05 (m, 28H, aromatic), 5.42-5.38 (dd, J=5.6 and 9.0 Hz, 1H, —CH₂—CH—N—), 4.68-4.64 (m, 2H, Bn—NH—), 3.62 (s, 4H, —N—(Bn)₂), 2.95 (br, 1H, —CH₂—CH—N—), 2.74-2.69 (m, 4H, —₃HCN—CH₂—, —CH₂—N(Bn)₂), 2.46-2.41 (m, 3H, —NCH₃), 1.57-1.19 (m, 7H, —CH₂—CH—N—, —CH₂—(CH₂)₃—CH₂—).

Example 18

Preparation of 4-(N-Benzylacetamino)-3-(4-Biphenylyl)-2-[N-(5-N',N'-Dimethylaminopentyl)-N-Methylamino]-3,4-Dihydroquinazoline (23) (KYS05090)

To a solution of N-benzyl-3-(4-biphenylyl)-2-[N-(5-N',N'-dibenzylaminopentyl)-N-methylamino]-3,4-dihydroquinazolin-4-ylacetamide (22) (530 mg, 0.73 mmol) and formalin solution (37%, 0.27 ml) in methanol (10 ml) was added 10% Pd(C) (120 mg), and the reaction mixture was stirred under hydrogen atmosphere for 24 hours. After the reaction was completed, the resulting reaction mixture was filtered with celite, extracted with dichloromethane three times, and washed with a saline solution. The combined organic phase was dried with anhydrous magnesium sulfate and distilled under reduced pressure. The resulting residue was subjected to silica gel column chromatography (eluent: dichloromethane:methanol:ammonia water=100:9:1) to give the target compound as a yellow liquid (260 mg, 62%).

$^1$H-NMR (400 MHz, CDCl$_3$) δ 7.72-6.98 (18H, m, Ph), 5.32 (1H, dd, J=9.1 and 4.6 Hz, COCH$_2$CH), 4.50 (2H, d, J=5.8 Hz, PhCH$_2$—), 3.50-3.20 (2H, m, CH$_3$N—CH$_2$), 2.71-2.33 (4H, CH$_3$—N and COCH), 2.44 (1H, dd, J=14.5 and 5.2 Hz, COCH), 2.30-2.29 (2H, m, —NCH$_2$), 2.21 (6H, s, 2×N—CH$_3$), 1.65-1.35(4H, m, 2×CH$_2$), 1.25-1.10 (2H, m, CH$_2$).

$^{13}$C NMR (400 MHz, CDCl$_3$) δ 170.1, 153.9, 145.3, 143.8, 140.4, 138.4, 136.7, 128.8, 128.6, 128.1, 128.0, 127.8, 127.4, 127.1, 127.0, 126.2, 125.1, 122.8, 122.4, 122.2, 61.2, 59.7, 49.5, 45.2, 43.8, 41.8, 35.3, 27.1, 27.0, 24.7.

MS (FAB+), m/z (relative intensity, %) 596.7([M+Na]$^+$, 100), 574.7([M+H]$^+$, 30); MS (FAB−), m/z (relative intensity, %) 572.7([M−H]$^+$, 100);

HRMS (FAB+) calcd for C$_{37}$H$_{44}$N$_5$O: [M+H]$^+$=574.3546, found=574.3516.

Example 19

Preparation of 2-[N-(5-Aminopentyl)-N-Methylamino]-3-(4-Biphenylyl)-4-Methoxycarbonylmethyl-3,4-Dihydroquinazoline (24) (KYS05096)

To a solution of 3-(4-biphenylyl)-2-[N-(5-dibenzylaminopentyl)-N-methylamino]-4-methoxycarbonylmethyl-3,4-dihydroquinazoline (19) (362 mg, 0.556 mmol) in methanol (20 ml) was added 10% Pd(C) (883 mg), and the reaction mixture was stirred under hydrogen atmosphere for 24 hours. After the reaction was completed, the resulting reaction mixture was filtered with celite, extracted with dichloromethane three times and washed with a saline solution. The combined organic phase was dried with anhydrous magnesium sulfate and distilled under reduced pressure. The resulting residue was subjected to silica gel column chromatography (eluent: dichloromethane:methanol:ammonia water=100:9:1) to give the target compound as a yellow liquid (110 mg, 42%).

$^1$H-NMR (400 MHz, CDCl$_3$) δ 7.52-6.88 (m, 13H, aromatic), 5.13-5.09 (dd, J=4.5 and 10.4 Hz, 1H, —CH$_2$—CH—N—), 3.75 (s, 3H, —OCH$_3$), 3.15 (br, 1H, —CH$_2$—CH—N—), 2.88-2.82 (m, 4H, —$_3$HCN—CH$_2$—, —CH$_2$—NH$_2$), 2.54-2.49 (dd, J=3.1 and 15.5 Hz, 1H, —CH$_2$—CH—N—), 2.25-2.23 (m, 3H, —NCH$_3$), 1.52-1.46 (m, 4H, —CH$_2$—CH$_2$—CH$_2$—CH$_2$—CH$_2$—NH$_2$), 1.26-1.23 (m, 2H, —(CH$_2$)$_2$—CH—(CH$_2$)$_2$—NH$_2$).

$^{13}$C NMR (400 MHz, CDCl$_3$) δ 171.9, 153.4, 145.4, 144.2, 140.4, 136.8, 128.8, 128.4, 127.9, 127.1, 126.8, 125.4, 124.8, 122.9, 122.6, 122.1, 61.2, 59.6, 51.9, 49.9, 45.3, 39.6, 35.5, 27.3, 24.8.

Example 20

Preparation of 4-(N-Benzylacetamino)-3-(4-Biphenylyl)-2-[N-(5-Aminopentyl)-N-Methylamino]-3,4-Dihydroquinazoline (25) (KYS05097)

To a solution of N-benzyl-3-(4-biphenylyl)-2-[N-(5-N',N'-dibenzylaminopentyl)-N-methylamino]-3,4-dihydroquinazolin-4-ylacetamide (22) (1.01 mmol) in methanol (20 ml) was added 10% Pd(C) (183 mg), and the reaction mixture was stirred under hydrogen atmosphere for 24 hours. After the reaction was completed, the resulting reaction mixture was filtered with celite, extracted with dichloromethane three times and washed with a saline solution. The combined organic phase was dried with anhydrous magnesium sulfate and distilled under reduced pressure. The resulting residue was subjected to silica gel column chromatography (eluent: dichloromethane:methanol:ammonia water=100:9:1) to give the target compound as a yellow liquid (304 mg, 55%).

$^1$H-NMR (400 MHz, CDCl$_3$) δ 7.72-6.98 (m, 18H, aromatic), 5.34-5.30 (dd, J=4.6 and 9.1 Hz, 1H, —CH$_2$—CH—N—), 4.51-4.49 (d, J=5.8 Hz, 2H, Bn—NH—), 2.72-2.66 (m, 4H, —$_3$HCN—CH$_2$—, —CH$_2$—NH$_2$), 2.47-2.42 (dd, J=5.1 and 14.5 Hz, 1H, —CH$_2$—CH—N—), 2.30-2.28 (m, 3H, —NCH$_3$), 1.47-1.24 (m, 7H, —CH$_2$—CH—N—, —CH$_2$—(CH$_2$)$_3$—CH$_2$—).

$^{13}$C NMR (400 MHz, CDCl$_3$) δ 170.1, 153.9, 145.3, 143.8, 140.4, 138.4, 136.7, 128.8, 128.6, 128.1, 128.0, 127.8, 127.4, 127.1, 127.0, 126.2, 125.1, 122.8, 122.4, 122.2, 61.2, 60.0, 49.5, 45.2, 43.8, 41.8, 35.3, 27.1, 24.7.

The chemical structures and physiochemical properties of the representative compounds of the present invention which were prepared in the above Examples are summarized in Table 1.

| No. | Physiochemical Properties |
|---|---|
| 14 | $^1$H NMR(300 MHz, CDCl$_3$) δ 7.58-7.41(6H, m, Ph), 7.36-7.11 (10H, m, Ph), 7.02-6.89(2H, m, Ph), 5.33(1H, dd, J=5.1, 9.6 Hz, —CO—CH$_2$—CH—N—), 4.51(2H, dd, J=3.3, 5.4 Hz, Ph—CH$_2$—NH—), 3.36(1H, br s, —NCH$_3$—CH$_2$—C$_4$H$_8$—), 2.76-2.56(10H, m, —NCH$_3$—CH$_2$—C$_4$H$_8$—, —NCH$_3$—CH$_2$—, —C$_4$H$_8$—CH$_2$-pyrrolidinyl-H2, H5, —CO—CH2—CH—N), 2.47(1H, dd, J=5.1, 14.4 Hz, —CO—CH$_2$—CH—N—), 1.80(4H, brs, -pyrrolidinyl-H3, H4), 1.52(4H, brs, —CH$_2$—CH$_2$—CH$_2$—CH$_2$—CH$_2$—), 1.35-1.29(2H, m, —C$_2$H$_4$—CH$_2$—C$_2$H$_4$—); $^{13}$C NMR(75 MHz, CDCl$_3$) δ 170.4, 154.2, 145.7, 144.2, 140.7, 138.7, 136.9, 129.0, 128.8, 128.3, 128.1, 127.6, 127.3, 127.0, 126.5, 125.4, 123.1, 122.6, 122.4, 61.4, 56.6, 54.3, 43.9, 41.9, 35.4, 30.0, 28.1, 27.2, 24.9, 23.5. |
| 23 | $^1$H-NMR(400 MHz, CDCl$_3$) δ 7.72-6.98(18H, m, Ph), 5.32(1H, dd, J=9.1 and 4.6 Hz, COCH$_2$CH), 4.50(2H, d, J=5.8 Hz, PhCH$_2$—), 3.50-3.20(2H, m, CH$_3$N—CH$_2$), 2.71-2.33(4H, CH$_3$—N and COCH), 2.44(1H, dd, J=14.5 and 5.2 Hz, COCH), 2.30-2.29(2H, m, —NCH$_2$), 2.21(6H, s, 2 x N—CH$_2$), 1.65-1.35(4H, m, 2 x CH$_2$), 1.25-1.10(2H, m, CH$_2$); $^{13}$C NMR(400 MHz, CDCl$_3$) δ 170.1, 153.9, 145.3, 143.8, 140.4, 138.4, 136.7, 128.8, 128.6, 128.1, 128.0, 127.8, 127.4, 127.1, 127.0, 126.2, 125.1, 122.8, 122.4, 122.2, 61.2, 59.7, 49.5, 45.2, 43.8, 41.8, 35.3, 27.1, 27.0, 24.7; MS(FAB+), m/z(relative intensity, %) 596.7([M + Na]$^+$, 100), 574.7([M + H]$^+$, 30); MS (FAB−), in/z(relative intensity, %) 572.7([M − H]$^+$, 100); BRMS(FAB+) calcd for C$_{37}$l$_{144}$N$_5$0: [M + H]$^+$ = 574.3546, found = 574.3516. |
| 25 | $^1$H-NMR(400 MHz, CDCl$_3$) δ 7.72-6.98(m, 18H, aromatic), 5.34-5.30(dd, J=4.6 and 9.1 Hz, 1H, —CH$_2$—CH—N—), 4.51 4.49(d, J=5.8 Hz, 2H, Bn—NH—), 2.72-2.66(m, 4H, —$_3$HCN—CH$_2$—, —CH$_2$—NH$_2$), 2.47-2.42(dd, J=5.1 and 14.5 Hz, 1H, —CH$_2$—CH—N—), 2.30-2.28(m, 3H, —NCH$_3$), 1.47-1.24(m, 7H, —CH$_2$—CH—N—, —CH$_2$—(CH$_2$)$_3$—CH$_2$—); $^{13}$C NMR(400 MHz, CDCl$_3$) δ 170.1, 153.9, 145.3, 143.8, 140.4, 138.4, 136.7, 128.8, 128.6, 128.1, 128.0, 127.8, 127.4, 127.1, 127.0, 126.2, 125.1, 122.8, 122.4, 122.2, 61.2, 60.0, 49.5, 45.2, 43.8, 41.8, 35.3, 27.1, 24.7. |

Compounds 14 (KYS05080), 23 (KYS05090), and 25 (KYS05097) have the following chemical structures:

| Compound | Structure |
|---|---|
| KYS05080 | 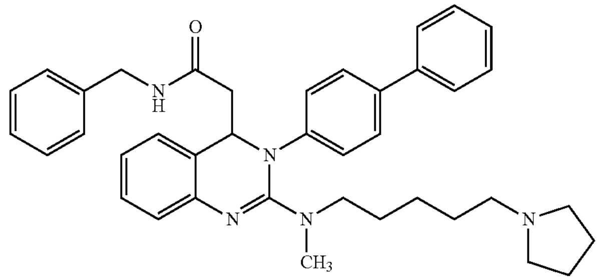 |
| KYS05090 | 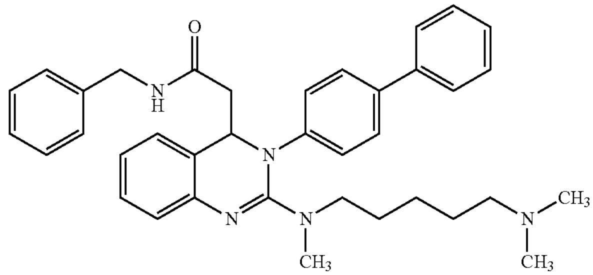 |
| KYS05097 | 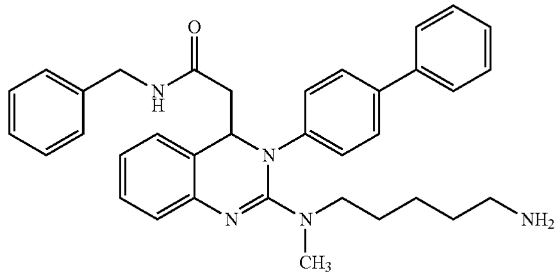 |

Biological Activity Test

T-type calcium channel blocking effects of the compounds of the present invention were tested according to an electrophysiological whole-cell patch-clamp method, which uses mammalian HEK293 cell line selectively expressing $\alpha_{1G}$ among T-type calcium channel encoding genes, wherein the $\alpha_{1G}$ is mainly expressed at nerve cells (derived from human kidney cancer cells), as described in Korean Patent No. 0610731 and Monteil, A., et al., *J. Biol. Chem.* 2000, 275, 6090-6100. Also, cytotoxicities of the compounds according to the present invention were tested according to a 3-(4,5-dimethylthiazol-2-yl)-2,5-diphenyltetrazolium bromide (MTT) assay. Further, growth inhibition effects against cancer cell lines of the compounds according to the present invention were tested according to a sulforhodamine B (SRB) assay, as disclosed in Skehan, P. et al., *J. Natl Cancer Inst.* 1990, 82, 1107-1112.

Experiment 1: Methods for Culturing HEK293 cells and measuring T-type Calcium Channel Activity Using an Electrophysiological Method HEK293 cells were cultured in Dulbecco's modified Eagle's medium (DMEM) supplemented with 10% fetal bovine serum (FBS) and 1% penicillin/streptomycin (v/v) in 36.5° C. humidified incubator (95% air-5% $CO_2$). The culture solution was replaced with a fresh medium every 3 to 4 days, and the cultured cells were subjected to sub-culture every week. At this time, the culture solution was treated with G-418 (0.5 mg/mL) solution so that only HEK293 cells expressing $\alpha_{1G}$ T-type calcium channel can grow. The cells used for T-type calcium channel activity assay were cultured on a cover slip coated with poly-L-lysine (0.5 mg/mL) whenever sub-cultured, and their calcium channel activity was recorded 2 to 7 days after the cultivation. Current of the T-type calcium channel at a single cell level was measured according to an electrophysiological whole-cell patch-clamp method using EPC-9 amplifier (HEKA, Germany). At this time, a cell exterior solution [NaCl 140 mM, $CaCl_2$ 2 mM, and HEPES (4-(2-hydroxyethyl)-1-piperazineethanesulfonic acid) 10 mM (pH 7.4)] and a cell interior solution [KCl 130 mM, HEPES 10 mM, EGTA (ethylene glycol tetraacetic acid) 11 mM, and MgATP 5 mM (pH 7.4)] were employed. Inward current caused by the T-type calcium channel activation which occurred when the cells were converted into a whole-cell recording mode by stabbing a microglass electrode having 3-4 MΩ resistance which was filled with the cell interior solution into a single cell and de-polarized at −30 mV (50 ms duration period) every 10 s with fixing membrane potential to −100 mV was measured according to a T-type calcium channel protocol activated at low current.

Experiment 2: Analysis for Cytotoxicities of T-type Calcium Channel Blockers Using MTT Assay In order to analyze cytotoxicities of the compounds according to the present invention in HEK293 cells, MTT [3-(4,5-dimethylthiazol-2-yl)-2,5-diphenyltetrazolium bromide] assay was conducted as follows. The cultured HEK293 cells were treated with each compound at a concentration of 10 and 100 µM, respectively. At this time, the cells treated with a solvent, that is, 0.1% DMSO, were used as a negative control and the cells treated with $H_2O_2$ (125 µM) inducing cytotoxicity were used as a positive control. Six hours after the drug treatment, the cells were treated with 50 µL MTT (1 mg/mL) dissolved in PBS (phosphate buffered saline) for 4 h. Then, the reaction mixture was centrifuged to remove a supernatant, and formazan crystals thus obtained were dissolved in 100 µL DMSO. The solution's absorbance was measured at 560 nm with an automated spectrophotometric plate reader. $CO_2$. The cells were seeded into 96-well plate. Various concentrations of compounds were added to each well in triplicate and then incubated at 37° C. with 5% $CO_2$ for 72 hours such that cells are in the exponential phase of growth at the time of drug addition. After incubation, 100 µL of formalin solution was gently added to the wells. Microplates were left for 30 min at room temperature and washed five times with tap water. One hundred microliters of 0.4% SRB solution was added to each well and left at room temperature for 30 min. SRB was removed and the plates were washed five times with 1% acetic acid before air-drying. Bound SRB was solubilized with 100 µL of 10 mM unbuffered Tris-base solution (Sigma) and plates were left on a plate shaker for at least 10 min. The optical density was measured using a microplate reader (Versamax, Molecular Devices) with a 520 nm wavelength and the growth inhibition concentration was expressed as $GI_{50}$.

The T-type calcium channel blocking effects and growth inhibition effects against cancer cell lines of the compounds according to the present invention, which were analyzed in the above Experiments, are summarized in Table 2.

TABLE 2

| Compound | Channel blocking effect ($IC_{50}$: µM)[a] T-type ($\alpha_{1G}$) | Growth inhibition of cancer cell: $GI_{50}$ (µM)[b] | | | | |
|---|---|---|---|---|---|---|
| | | A-549[c] | DU 145[d] | HT-29[e] | SK-MEL-2[f] | SK-OV-3[g] |
| (KYS05042) | 0.11 ± 0.06 | 1.93 ± 0.13 | 1.71 ± 0.16 | 1.71 ± 0.17 | 1.73 ± 0.28 | 1.95 ± 0.23 |
| (KYS05043) | 0.30 ± 0.09 | 2.90 ± 0.38 | 4.09 ± 0.71 | 1.08 ± 0.28 | 1.80 ± 0.48 | 3.99 ± 1.07 |
| (KYS05046) | 0.68 ± 0.18 | 3.83 ± 0.55 | 3.83 ± 1.08 | 2.08 ± 0.43 | 4.31 ± 2.56 | 4.61 ± 0.30 |
| (KYS05047) | 0.17 ± 0.03 | 1.87 ± 0.05 | 1.79 ± 0.04 | 1.70 ± 0.16 | 1.59 ± 0.27 | 2.01 ± 0.32 |
| (KYS05048) | 0.16 ± 0.02 | 1.83 ± 0.22 | 1.64 ± 0.09 | 1.67 ± 0.18 | 1.48 ± 0.31 | 1.61 ± 0.09 |
| (KYS05055) | 0.35 ± 0.07 | >100 | >100 | 22.31 ± 1.00 | 31.62 ± 3.05 | >100 |
| (KYS05056) | 0.38 ± 0.15 | >100 | >100 | 28.28 ± 1.42 | 43.95 ± 7.68 | >100 |
| (KYS05057) | 0.63 ± 0.04 | 14.27 ± 1.05 | 6.52 ± 1.00 | 3.15 ± 0.66 | 8.53 ± 1.65 | 15.61 ± 1.14 |
| (KYS05065) | 1.04 ± 0.25 | 24.46 ± 5.79 | 17.21 ± 1.39 | 13.94 ± 1.13 | 17.03 ± 1.56 | 26.14 ± 6.08 |
| (KYS05080) | 0.26 ± 0.01 | 0.87 ± 0.18 | 2.49 ± 0.53 | 0.61 ± 0.12 | 0.69 ± 0.15 | 2.76 ± 0.76 |
| (KYS05085) | 0.57 ± 0.05 | 7.74 ± 2.60 | 4.26 ± 0.56 | 3.18 ± 0.52 | 2.02 ± 0.40 | 7.18 ± 1.18 |
| (KYS05089) | 0.23 ± 0.03 | 1.77 ± 0.16 | 1.78 ± 0.17 | 0.52 ± 0.24 | 1.91 ± 0.11 | 1.95 ± 0.04 |
| (KYS05090) | 0.041 ± 0.001 | 0.17 ± 0.02 | 0.19 ± 0.02 | 0.04 ± 0.01 | 0.48 ± 0.13 | 0.66 ± 0.13 |
| Doxorubicin | ND[h] | 0.16 ± 0.01 | 0.06 ± 0.01 | 0.21 ± 0.04 | 0.11 ± 0.01 | 0.12 ± 0.02 |

[a]Value was determined from dose-response curve and obtained from three independent experiments.
[b]$GI_{50}$ value was determined from dose-response curve and obtained from three independent experiments.
[c]Human lung carcinoma (A-549).
[d]Human prostate cancer (DU 145).
[e]Human colon cancer (HT-29).
[f]Human malignant melanoma (SK-MEL-2).
[g]Human ovarian cancer (SK-OV-3).
[h]ND: not determined As a result, the compounds of the present invention did not show any cytotoxicity at a concentration of 100 µM.

Experiment 3: Analysis for Growth Inhibition Against Cancer Cell Lines Using SRB Assay The compounds according to the present invention were evaluated for their growth inhibition against five cancer cell lines, including human lung carcinoma (A-549), human prostate cancer (DU 145), human colon cancer (HT-29), human malignant melanoma (SK-MEL-2) and human ovarian cancer (SK-OV-3) using sulforhodamine B (SRB) assay. All cell lines were grown in RPMI 1640 (Gibco BRL) supplemented with 10% (v/v) heat-inactivated fetal bovine serum (FBS) and maintained at 37° C. in a humidified atmosphere with 5%

The biological activities of doxorubicin and KYS05042 disclosed in Korean Patent No. 0610731 were evaluated as references, and the results are indicated in Table 2. As shown in Table 2, a compound of the present invention, KYS05090 showed nearly equipotent growth inhibition and exhibited about 5 times stronger activity against human colon cancer cell line, compared to doxorubicin. Moreover, KYS05090 showed about 10 times stronger growth inhibition and exhibited about 40 times stronger activity against human colon cancer cell line, compared to KYS05042.

The invention claimed is:
1. A compound of formula (I) or pharmaceutically acceptable salt thereof:

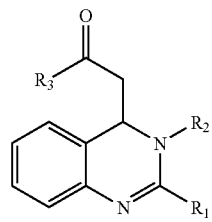

wherein, $R_1$ is $NR_4(CH_2)_nNR_5R_6$, wherein $R_4$ is a $C_1$-$C_5$ alkyl, n is 5, $R_5$ and $R_6$ are identical and a $C_1$-$C_5$ alkyl;

$R_2$ is 4-biphenylyl; and $R_3$ is benzylamino or 4-aminobenzylamino.

2. The compound according to claim 1 or pharmaceutically acceptable salt thereof, wherein the compound is 4-(N-benzylacetamino)-3-(4-biphenylyl)-2-[N-(5-N',N'-dimethylaminopentyl)-N-methylamino]-3,4-dihydroquinazoline.

3. A pharmaceutical composition comprising the compound of formula (I) according to claim 1 or pharmaceutically acceptable salt thereof together with a pharmaceutically acceptable carrier.

* * * * *